(12) United States Patent
Makdissi

(10) Patent No.: US 11,013,926 B2
(45) Date of Patent: May 25, 2021

(54) ACTIVE IMPLANTABLE MEDICAL DEVICE WITH DYNAMIC OPTIMIZATION OF STIMULATION PULSE ENERGY

(71) Applicant: SORIN CRM SAS, Clamart (FR)

(72) Inventor: Alaa Makdissi, Paris (FR)

(73) Assignee: Sorin CRM SAS, Clamart (FR)

( * ) Notice: Subject to any disclaimer, the term of this patent is extended or adjusted under 35 U.S.C. 154(b) by 235 days.

(21) Appl. No.: 15/936,111

(22) Filed: Mar. 26, 2018

(65) Prior Publication Data
US 2018/0214702 A1   Aug. 2, 2018

Related U.S. Application Data

(63) Continuation of application No. 14/992,677, filed on Jan. 11, 2016, now Pat. No. 9,925,383.

(30) Foreign Application Priority Data

Jan. 12, 2015 (FR) ........................................ 1550203

(51) Int. Cl.
*A61N 1/37* (2006.01)
*A61N 1/05* (2006.01)
*A61N 1/372* (2006.01)

(52) U.S. Cl.
CPC .......... *A61N 1/3712* (2013.01); *A61N 1/056* (2013.01); *A61N 1/37205* (2013.01)

(58) Field of Classification Search
CPC ... A61N 1/3712; A61N 1/056; A61N 1/37205
USPC ........................................................... 607/28
See application file for complete search history.

(56) References Cited

U.S. PATENT DOCUMENTS

| | | | |
|---|---|---|---|
| 3,777,762 A | 12/1973 | Nielsen | |
| 4,979,507 A | 12/1990 | Heinz et al. | |
| 5,350,410 A * | 9/1994 | Kleks | A61N 1/3712 607/11 |
| 5,549,652 A | 8/1996 | McClure et al. | |

(Continued)

FOREIGN PATENT DOCUMENTS

| | | |
|---|---|---|
| EP | 0 552 357 A1 | 7/1993 |
| EP | 2 412 401 A1 | 2/2012 |

(Continued)

OTHER PUBLICATIONS

Preliminary Search Report for French Patent Application No. 1550203, dated May 26, 2015, 2 pages.

*Primary Examiner* — Erin M Piateski
(74) *Attorney, Agent, or Firm* — Foley & Lardner LLP

(57) ABSTRACT

The disclosure relates to a device including a circuit for adjusting the energy of the stimulation pulses, independently controlling the pulse width and the voltage of each stimulation pulse. An iterative search algorithm for determining the optimum energy includes changing both the pulse width and voltage at each new pulse delivered, by setting a high energy value and a low energy value, and delivering a stimulation pulse with the low energy value. A capture test is then carried out. In the presence of a capture, a current iteration is complete and a new iteration is done with the current low energy as a new high energy value. In the absence of capture, the algorithm is terminated with selection of the last energy value that produced the capture as the value of optimum energy.

20 Claims, 4 Drawing Sheets

(56) References Cited

U.S. PATENT DOCUMENTS

| | | | |
|---|---|---|---|
| 5,697,956 A * | 12/1997 | Bornzin | A61N 1/3712 607/28 |
| 5,702,427 A | 12/1997 | Ecker et al. | |
| 5,718,720 A | 2/1998 | Prutchi et al. | |
| 6,650,940 B1 | 11/2003 | Zhu et al. | |
| 6,738,668 B1 | 5/2004 | Mouchawar et al. | |
| 8,666,490 B1 * | 3/2014 | Ryu | A61N 1/3712 607/28 |
| 2004/0064162 A1 | 4/2004 | Manrodt et al. | |
| 2006/0129193 A1 | 6/2006 | Zhang | |
| 2011/0245890 A1 * | 10/2011 | Brisben | A61N 1/3712 607/28 |

FOREIGN PATENT DOCUMENTS

| | | |
|---|---|---|
| WO | WO-94/12237 | 6/1994 |
| WO | WO-95/34343 | 12/1995 |

* cited by examiner

ACTIVE IMPLANTABLE MEDICAL DEVICE WITH DYNAMIC OPTIMIZATION OF STIMULATION PULSE ENERGY

CROSS-REFERENCE TO RELATED PATENT APPLICATIONS

This application is a continuation of U.S. patent application Ser. No. 14/992,667, filed Jan. 11, 2016, now U.S. Pat. No. 9,925,383, issued Mar. 27, 2018, which claims the benefit of and priority to French Patent Application No. 1550203, filed Jan. 12, 2015, the disclosures of both are incorporated by reference herein in their entirety.

BACKGROUND

The invention relates to "active implantable medical devices" as defined by the Directive 90/385/EEC of 20 Jun. 1990 of the Council of the European Communities, and particularly to implantable devices that continuously monitor heart rate and if necessary deliver electrical stimulation, resynchronization and/or defibrillation pulses to the heart in case of rhythm disorder detected by the device.

The invention relates especially, but is not limited to, those devices that are in the form of an autonomous capsule intended to be implanted in a heart chamber, including the ventricle.

These capsules are free of any mechanical connection to an implantable (such as a housing of the stimulation pulse generator) or non-implantable (external device such as programmer or monitoring device for patient remote monitoring) main device, and for this reason are called "leadless capsules" to distinguish the capsules from electrodes or sensors disposed at the distal end of a conventional probe (lead), which is traversed throughout its length by one or more conductors galvanically connecting the electrode or sensor to a generator connected to an opposite, proximal end of the lead. A detection/stimulation electrode in contact with the wall of the ventricle enables the capsule to detect the presence or absence of a spontaneous depolarization wave of the cardiac cavity, as well as the occurrence time of the wave (ventricular or atrial marker).

The electrode also allows the delivery of a stimulation pulse in the event of absent or late spontaneous depolarization, so as to cause contraction of the cardiac cavity.

Note, however, that the autonomous nature of the capsule is not inherently a necessary feature of the present invention.

The management of the stimulation energy is a critical aspect of any implantable pacemaker, because it has a direct impact on the power consumption of the integrated pacemaker battery, and thus on its overall lifespan.

This topic is particularly critical in the case of a leadless capsule pacemaker wherein, unlike conventional pacemakers, the energy required for the issuance of stimulation is 70% of the total energy consumed. In addition, it must be considered that the very small dimensions of a leadless capsule imposes minimizing the size of the battery and thus its capacity, as the battery often occupies more than 70% of the volume in a leadless capsule.

In fact, if it was possible to reduce, for example, half the energy required for stimulation, the size of the battery could correlatively be reduced about 40% while keeping the same longevity, which would reduce the volume of the capsule to about 0.6 cm$^3$ (compared to 1 cm$^3$ in the best case today), all performances being equal.

To minimize the energy dedicated to stimulation as much as possible, while maintaining the effectiveness of delivered electrical pulses, a technique called "cycle to cycle capture" may be employed. Cycle to cycle capture maintains the stimulation energy at a minimum level, continuously checking, after each stimulation, if the stimulation was effective ("capture") or not. If no depolarization wave has been induced by stimulation of the cardiac cavity ("non-capture"), the implant delivers, during the same cardiac cycle, a stimulation of a relatively high energy to ensure the triggering of a depolarization. Then, by successive iterations, the stimulation energy is gradually reduced in each cardiac cycle, so as to converge again to an energy close to the limit or "triggering threshold" needed to cause depolarization of the cardiac cavity.

The invention relates more precisely to a method to determine the pacing threshold by successive approaches, in the most efficient possible method from the energy consumption point of view.

The basic technique which is commonly used today in most pacemakers, is described in U.S. Pat. No. 3,777,762 A. The technique involves using a method of progressive decreases in amplitude (voltage) of the stimulation pulses for a fixed pulse width.

Another technique is described in U.S. Pat. No. 4,979,507 A. This technique relies on the fact that the delivered energy not only depends on the amplitude of the stimulation pulses, but also of the width of these pulses (stimulation duration). The pacing threshold varies as a function of these two parameters according to a nonlinear law called "Lapicque law".

The technique proposed in U.S. Pat. No. 4,979,507 A includes performing two amplitude scans, with two different pulse widths. This approach has a risk of capture default, because the theoretical Lapicque law defines a boundary between capture and non-capture that, in practice, varies from one patient to another. It is therefore necessary to validate either continuously or at regular intervals the method for each patient, by making a complete scan of all possible values of the parameters (amplitude and width of the stimulation pulse). However, a full scan is impractical because it is very costly in terms of energy and requires interrupting therapy during scanning.

WO 94/12237 A1 discloses another technique for automatically adjusting the capture threshold wherein, again, the variation of the energy of one stimulation pulse to the next is made either by changing the duration of the pulse, or by changing the amplitude of the pulse. This significantly increases the number of iterations required for the search algorithm to determine the actual value of the stimulation threshold.

U.S. Pat. Nos. 5,718,720 A, 5,702,427 A, 5,549,652 A and 6,650,940 B1 describe other techniques for determining the pacing threshold, implementing various capture detection methods such as a direct detection of mechanical myocardial contraction, analysis of an accelerometric signal, analysis of a temperature signal, analysis of intracardiac pressure, etc.

SUMMARY

The object of the disclosure is to provide a new technology to search for an optimum of both parameters defining the energy delivered by the stimulation pulse, namely the stimulation voltage (the amplitude of the pulse) and the duration of the stimulation (the width of the pulse), in both the fastest and the most energy consumption saving method.

The problem to solve is minimizing the number of stimulations to deliver to determine the pacing threshold, so as to consequently reduce the power consumption of the implant in order to improve the overall lifespan.

The starting point of the disclosure is, in contrast to known search techniques which typically operate by scanning successive amplitude values for a given pulse width, simultaneously executing a search algorithm in two dimensions (width and amplitude pulse). This algorithm allows for the possibility of varying both parameters of a stimulation pulse to the next stimulation pulse according to a mechanism that depends on the result (presence or absence of capture) of the previous stimulation.

As will also be seen, the disclosure provides such an algorithm iteratively operating by dichotomy, on the basis of a minimization of the total energy of the pulse, and not only the minimization of the voltage of the pulse.

More specifically, the invention proposes an active implantable medical device including:

a ventricular stimulation circuit adapted to deliver low energy pacing pulses to an implantable electrode within a heart chamber of a patient;

a capture test circuit adapted to detect, during a cardiac cycle, the presence or absence of a contraction subsequent to the application of a stimulation pulse; and an adjusting circuit capable of independently controlling the stimulation voltage and the stimulation pulse width of the energy pulses delivered by the stimulation circuit.

In one embodiment, the adjustment circuit is configured to implement an iterative algorithm to re-search for optimum energy and is capable of modifying both the pulse width t and the voltage V of each new delivered pulse. The adjustment circuit is configured to, at each current iteration, perform the following actions:

set a value $\{t,V\}$ of high energy;

set a value $\{t',V'\}$ of low energy, with $t'<t$ and $V'<V$;

deliver a pacing pulse with the low energy value, then perform a capture test; and in the presence of a capture, end the current iteration and transition to a new iteration, with the current low energy as the new high energy value, in the absence of capture, i) apply a consecutive r stimulation pulse of pulse width t and of voltage V defined for said high energy value, and ii) the algorithm and select the last energy value that produced the capture as the optimum energy value.

In a preferred embodiment, the adjustment circuit is further configured to perform the following actions:

set a first intermediate energy value $\{t',V\}$;

set a second intermediate energy value $\{t,V'\}$;

set a third intermediate energy value $\{t'',V''\}$, with $t'<t''<t$ and $V'<V''<V$ rank the first, second and third intermediate energy values by decreasing energy value; and in the absence of capture after delivery of the pulse with low energy value and capture test, continue the current iteration with delivery of pacing pulses in succession with the first, second and third intermediate energy values sorted by decreasing value of energy to detect a capture; and in the presence of a capture, end of the current iteration and transition to a new iteration with the current intermediate energy that produced the capture as a new high energy value, in the absence of capture, complete the algorithm and selection of the last value of energy produced with the capture among the first, second and third intermediate energy values as the optimum energy value.

The third intermediate energy value may be a value $\{t'',V''\}$ such that $t''=(t+t')/2$ and $V''=(V+V')/2$.

According to various advantageous subsidiary embodiments:

the energy values of the pulses delivered by the stimulation circuit are, at most, equal to a maximum energy limit value, and the high energy value $\{t,V\}$ in the first iteration of the algorithm is the maximum energy limit value;

the energy values of the pulses delivered by the stimulation circuit are at least equal to a minimum energy limit value $\{tL,VL\}$ (L), wherein said low energy value is a value $\{t',V'\}$ such that $t'=(t+tL)/2$ and $V'=(V+VL)/2$;

the energy values of the pulses delivered by the stimulation circuit are between a maximum energy limit value and a minimum energy limit value calculated before each first iteration of the algorithm;

in the latter case, the pulse width and the voltage of the maximum energy value and of the minimum energy value are calculated by the application of multiplication factors, respectively the upper and lower unit of the current pulse width and of the current voltage of the stimulation circuit before the first iteration of the algorithm.

BRIEF DESCRIPTION OF THE DRAWINGS

Further features, characteristics and advantages of the present invention will become apparent to a person of ordinary skill in the art from the following detailed description of preferred embodiments of the present invention, made with reference to the drawings annexed, in which like reference characters refer to like elements and in which.

DETAILED DESCRIPTION

An exemplary embodiment of the device of the disclosure will now be described.

Regarding its software aspects, the disclosure may be implemented by appropriate programming of the controlling software of a known cardiac pacemaker, for example an endocardial leadless capsule.

These devices include a programmable microprocessor provided with circuits for shaping and delivering stimulation pulses to implanted electrodes. It is possible to transmit software to the device by telemetry that will be stored in memory and executed to implement the functions of the disclosure which will be described below. The adaptation of these devices to implement the functions of the disclosure is within the reach of a skilled-in-the-art person and will not be described in detail. In particular, software stored in memory and executed can be adapted and used to implement the functions of the disclosure which will be described below.

The method of the disclosure is implemented primarily by software, through appropriate algorithms performed by a microcontroller or a digital signal processor. For the sake of clarity, the various processing applied will be decomposed and schematized by a number of separate functional blocks in the form of interconnected circuits, but this representation, however, is only illustrative, these circuits including common elements in practice correspond to a plurality of functions generally performed by the same software.

Figure 1:
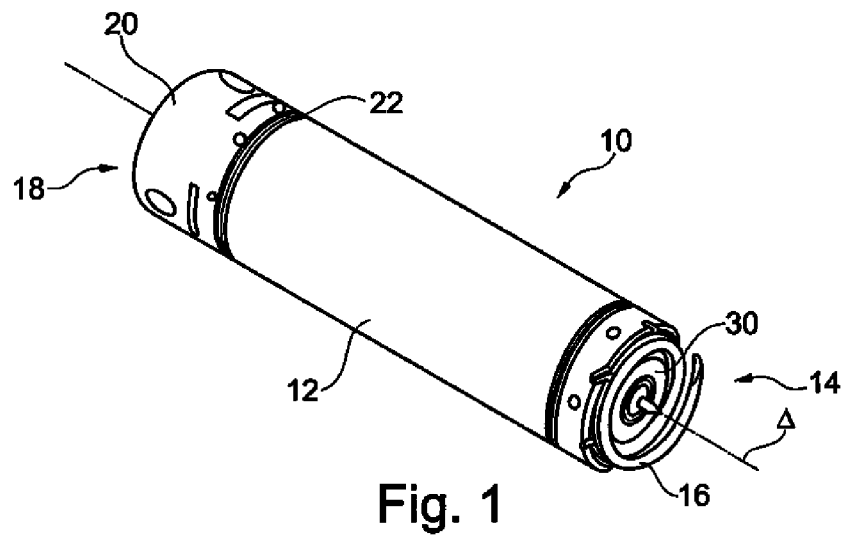
FIG. 1 is an overall perspective view of a leadless capsule.
Figure 2:
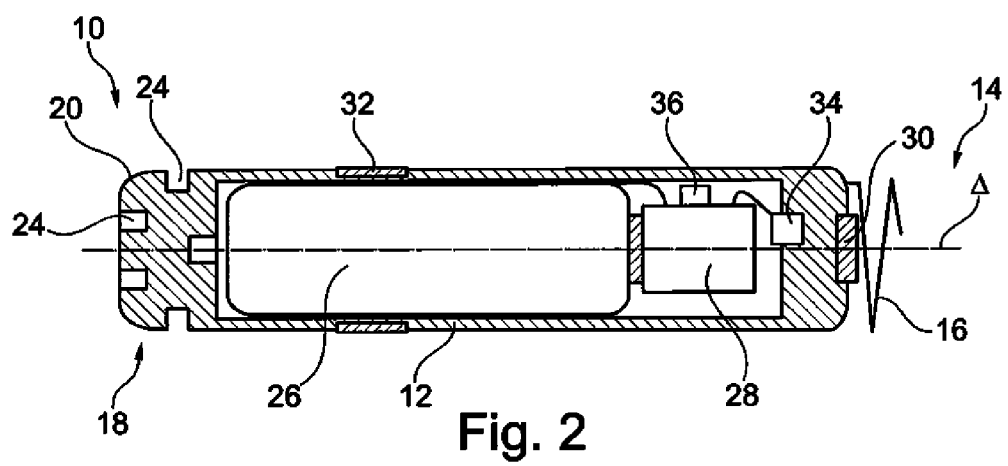
FIG. 2 is a longitudinal cross sectional view of the leadless capsule of FIG. 1 showing the main internal components.

FIGS. 1 and 2 respectively show, in perspective and in longitudinal cross section, an example of a leadless capsule.

In these figures, the reference 10 generally designates the capsule, formed as a cylindrical tubular body 12 of axis Δ enclosing the various electronic circuits and power supply of the capsule. Typical dimensions of such a capsule are a diameter of about 6 mm and a length of about 25 mm.

At its distal end 14, the capsule includes a helical anchoring screw 16 for fixing the capsule into tissue, for example against a wall of a heart chamber. The helical anchoring screw 16 can optionally be an active, electrically conductive screw for collecting the potential of cardiac depolarization and/or for the application of stimulation pulses. The proximal region 18 of the capsule 10 has a rounded, atraumatic end 20 and is provided with grips 22, 24 suitable for implantation or removal of the capsule.

As shown in FIG. 2, the capsule 10 incorporates a battery 26, typically with a volumetric energy density of the order of 0.8 to 2 kg/cm$^3$, an electronic module 28, a front electrode 30, and optionally a side electrode 32. Feedthroughs such as 34 are used to connect the electrodes to the electronic module 28.

The electronic module 28 includes all of the electronics for controlling the various functions of the implant, storing the collected signals, etc. It includes a microcontroller and an oscillator generating the clock signals necessary to the operation of the microcontroller and communication. It also contains an analog/digital converter and a digital storage memory. It may also contain a transmitter/receiver for exchanging information with other implantable devices by HBC (Human Body Communication, intracorporeal communication) communication.

The capsule 10 also includes a endocardial acceleration (EA) sensor 36 capable of delivering a signal representative of the mechanical activity of the myocardium, for example a microaccelerometer shaped sensor interfaced with the electronic module 28.

The sensor of EA signal 36 can be a 1D, 2D or 3D accelerometric sensor. Preferably, the sensor is a piezoelectric or a capacitive sensor, but other types of sensors (optical, resistive, inductive, etc.) capable of generating a signal correlated to the displacement, velocity or acceleration of the heart walls may be used.

Figure 3:
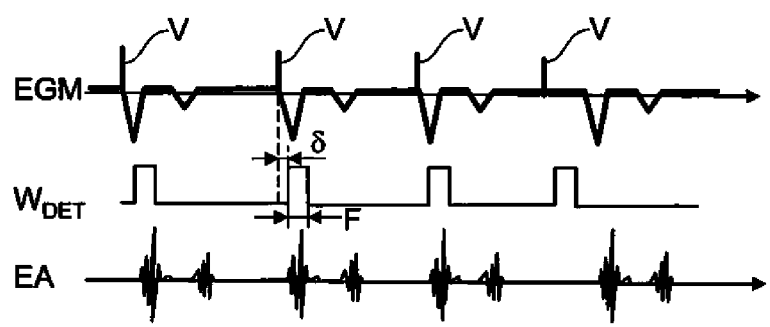
FIG. 3 is a series of timing diagrams illustrating an electrogram EGM signal, the detection windows for the capture test and the endocardial acceleration EA signal.

FIG. 3 shows a series of timing diagrams illustrating an electrogram (EGM) signal, detection windows $W_{DET}$ for the capture test, and the endocardial acceleration (EA) signal.

After each stimulation (marker V of stimulated depolarization on the EGM), the measurement of the EA signal delivered by the accelerometer is activated for a $W_{DET}$ window which is open either immediately after the issuance of the stimulation pulse, or with a delay δ on the order of 5 to 100 ms. The length F of the window $W_{DET}$ is between 75 and 350 ms. Controlling the start time of the capture window $W_{DET}$ and its duration is achieved via a sequencing circuit of the microcontroller and the embedded software which controls the electronic circuits of the implant.

EP 2412401 A1 (Sorin CRM) discloses a capture test technique by analyzing a signal EA, including successive components (EA components) of the signal which correspond to the major heart sounds that can be recognized in each cardiac cycle (S1 and S2 sounds of a phonocardiogram). The amplitude variations of the first component (EA1 component) are closely related to changes in pressure in the ventricle, while the second component (EA2 component) occurs during the isovolumetric ventricular relaxation phase. The analysis can also take into account the secondary component (called EA4 or EA0) produced by the contraction of the atrium.

These components are analyzed to extract various relevant parameters such as the peak-to-peak of the PEA1 and PEA2 peaks of the EA1 and EA2 components, the temporal interval between these PEA1 and PEA2 peaks, the half-height width of the EA1 and/or EA2 components, the instants of beginning and ending of these components, etc. It may also be representative of morphological parameters of the waveform of the EA signal or of its envelope.

This capture technique by analyzing an EA signal is not, however, limitative of the disclosure and one can for example proceed as described for example in EP 0552357 A1 (ELA Medical) by analysis of EGM signals of depolarization of the myocardium to recognize the presence or absence of an evoked wave consecutive to the application of the stimulation pulse.

The basic concept of the disclosure, unlike known techniques which often operate a scanning of the amplitude of the stimulation pulse at constant pulse width, is to operate a search algorithm simultaneously in two dimensions (amplitude and pulse width).

The energy expended by the delivery of a stimulation pulse amplitude of voltage V and of width t is given by:

$$E(V, t) = \frac{V^2 t}{R}$$

R being the impedance of the heart tissue between the two stimulation electrodes.

Figure 4:
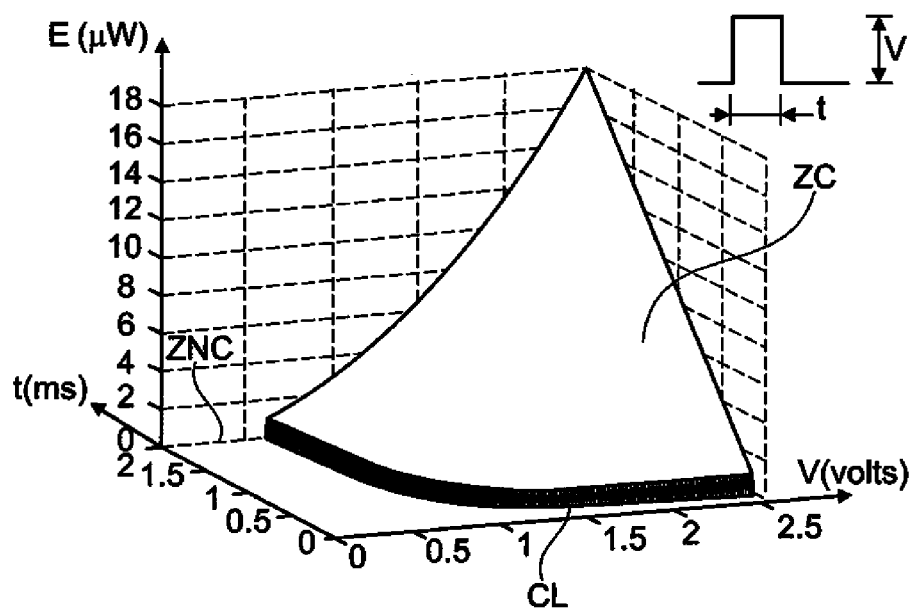
FIG. 4 is a three-dimensional representation of the energy expended by the application of a stimulation pulse, depending on the amplitude and width of the stimulation pulse.

FIG. 4 shows the variation of the energy E expended by a pacing pulse as a function of the two parameters V and t. This representation includes two areas, with a capture zone ZC, wherein the energy delivered is sufficient to cause myocardial contraction, and a non-capture area ZNC, wherein this stimulation energy was not sufficient to cause myocardial contraction. These two zones are separated by a border CL, corresponding to the theoretical Lapicque's curve, which is a nonlinear theoretical boundary that may vary from one patient to another. In the capture zone ZC, the stimulation energy increases with the voltage and the pulse width, according to a nonlinear relation.

The energy E(V, t) is the power actually dissipated in the impedance R, that is to say, in the heart tissue. The energy actually consumed by the electric power source, $E_p(V, t)$, of the implant (battery or rechargeable battery) is equal to:

$$E_p(V, t) = \frac{V^2 t}{\eta(V) R}$$

wherein η(V) is the yield of the circuit for generating the stimulation voltage V.

The search technique of optimum energy by dichotomy according to the disclosure will now be explained with reference to FIG. 5.

The purpose is to achieve, in a minimum number of steps, the stimulation conditions (pulse amplitude and width) that minimize the energy necessary for the issue of pulses providing an effective capture.

It is assumed that the stimulation circuit is adjusted at a given instant, with current pacing parameters $t_c$ and $V_c$ corresponding at point S of coordinates $\{t_c, V_c\}$.

Point L represents the minimum pacing energy value to be tested during the research phase, this point preferably being defined according to the point S (the position L is not fixed but depends on the current stimulation energy):

$$\vec{L} = (\alpha_1 t_c, \alpha_2 V_c)$$

wherein α1 and α2 are constants lower than unity. Typical values for α1 and α2 are, for example, α1=α2=2/3. Other values closer to zero could help the search of points with lower energy, but with a longer search phase (energetically more expensive).

In the case of loss of capture at the current point S (which is the case in the example of FIG. 5, since the point S is located below the Lapicque's curve CL for the considered patient (the curve that defines the border between capture zones ZC and non-capture zones ZNC)), a rectangular window ADBC is defined, from both points A and B.

Point B is chosen such that:

$$\vec{B} = (\beta_1 t_c, \beta_2 V_c)$$

wherein β1 and β2 are constant superior to unity.

Point B establishes a maximum energy limit to be tested in the search phase, which is energy dependent, as the minimum energy at the point L, on the position of the current point S. Point B is determined to correspond to an energy wherein it is certain that the stimulation will be effective, which is the case if, for example, β1=4 and β2=2.

Point A is chosen as the middle of the segment LB:

$$\vec{A} = \frac{\vec{L} + \vec{B}}{2}$$

Point M is defined as the center of the rectangle ADBC:

$$\vec{M} = \frac{\vec{A} + \vec{B}}{2}$$

Point D of the rectangle ADBC is the point defined by $t_D = t_A$, and $V_D = V_B$, and point C is the point defined by $t_C = t_B$ and $V_C = V_A$ (ADBC the being a rectangle domain).

Four test points are defined to implement the search algorithm, namely points A, M, C and D. Point B will be considered a "rescue point" in case of detection of lack of capture. The device immediately applies a counter-stimulation with an energy corresponding to that of point B to compensate for loss of capture and to be certain that the counter-stimulation pulse is a capturing pulse.

The search for the best point of the four test points A, M, C and D is performed in the order of increasing energy cost, with iterations of the search algorithm according to the following steps:

1) The standby point B' of the possible next iteration of the search algorithm is defined, which will be point B'=B;
2) Point A is tested first because it costs less energy than the other points D, M or C, the voltage and/or amplitude being lower in A than in the three other points. Therefore stimulation with the energy corresponding to the point A is applied;
3) If a capture is detected during the test at point A, the following points D, M and C are not tested, and a new rectangle A'D'B'C' is defined with B'=A, its center being M';
4) In case of lack of capture during the test at point A, we calculate energy values proportional to the theoretical energy that stimulation at points D, M and C cost, according to the formula $E_p(i) = V(i)*V(i)*t(i)$, i being a point among D, M and C.
5) The three points D, M and C are classified according to the values $E_p(i)$ calculated in the preceding step, in descending order, which gives three points X1, X2 and X3 such that:

$$[X1, X2, X3] = \text{tri}(\{D, M, C\}), \text{ with } E_p(X1) < E_p(X2) < E_p(X3)$$

6) Point X1 is then tested. If a capture is detected, no test is carried out on the point X2 and X3 and a new rectangle is defined, with B'=X1;
7) In the opposite case, a counter-stimulation is applied (point B) to compensate for loss of capture, and then point X2 is tested at the next cycle;
8) If a capture is detected at point X2, no test is performed on point X3 and a new rectangle is defined, with B'=X2;
9) Otherwise, a counter-stimulation is applied (point B) to compensate the loss of capture and then point X3 is tested at the next cycle;
10) If a capture is detected at the point X3, a new rectangle is defined, with B'=X3;
11) If a capture was detected at one of the points X1, X2 or X3, the above procedure of steps 1) to 10) is iterated, with B=B' and A=(L+B)/2, that is to say that A is the midpoint of segment LB';
12) If after any reiteration of test no point has produced capture, then the search algorithm is terminated and the last point B that produced the capture is defined as the optimal energy value.

In a simplified variant, the algorithm is stopped after the first test point which causes a loss of capture. The number of steps can thus be reduced, resulting in less energy consumed.

Figure 5:
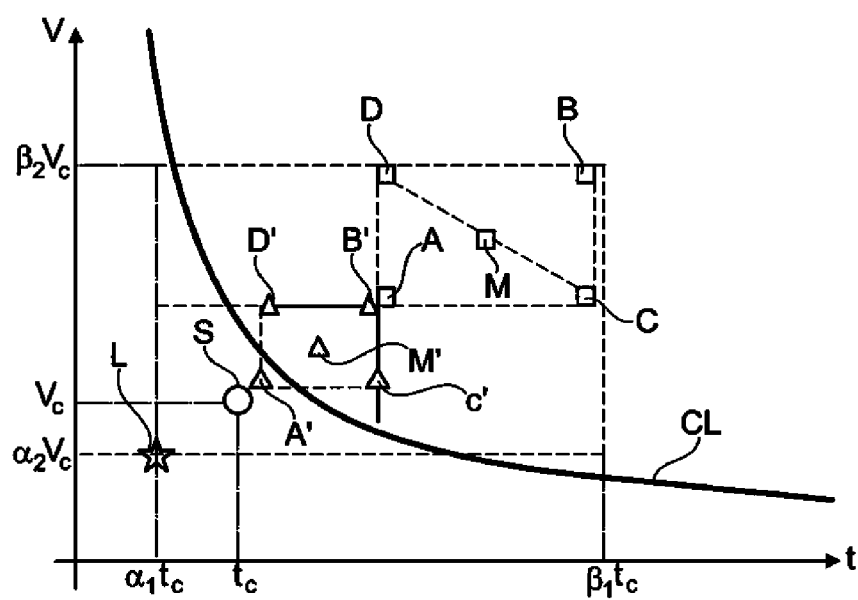
FIG. 5 is a two dimensional representation, as a function of the amplitude and the width of successive stimulation pulses, of the dichotomy search technique according to the disclosure, with, for each iteration, concurrently changing the amplitude and the width of the delivered pulse.
Figure 6:
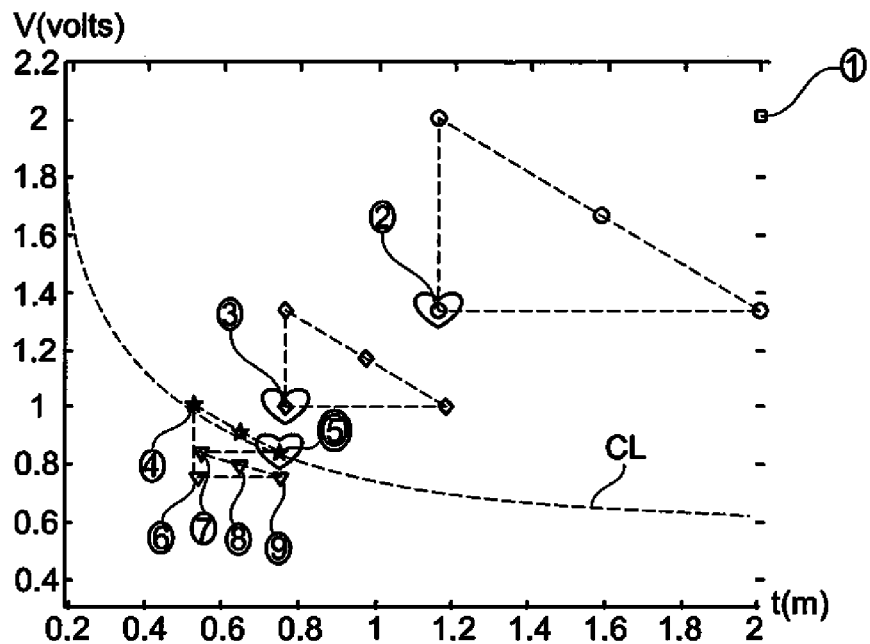
FIG. 6 is a representation of the algorithm of FIG. 5 applied to a first illustrative implementation.
Figure 7:
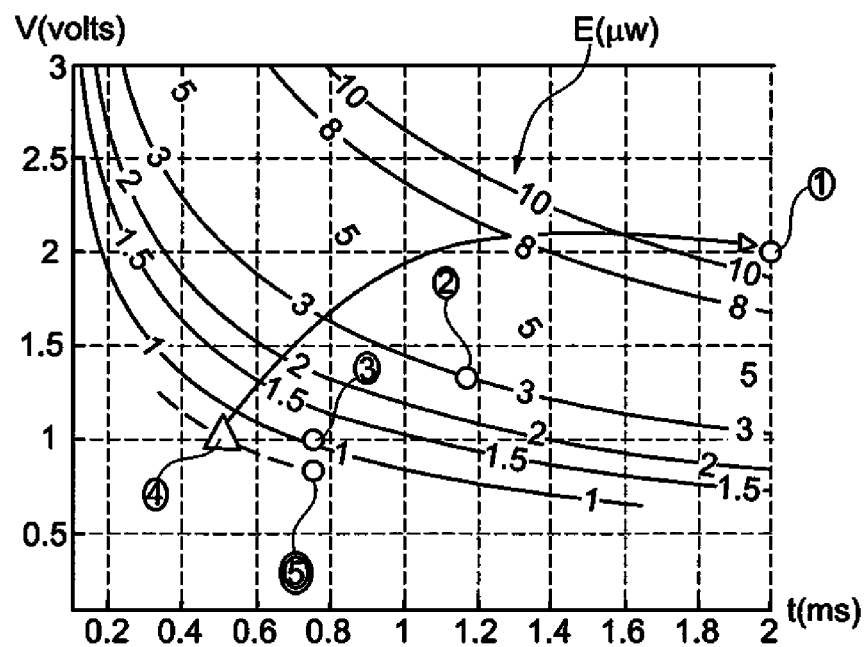
FIG. 7 is a voltage/pulse width diagram corresponding to the example of FIG. 6, to which isoenergetic curves have been added.

FIGS. 6 and 7 are representations of the algorithm of FIG. 5 applied to a first illustrative implementation (on FIG. 7, the isoenergetic curves were added to the representation of FIG. 6).

Successive test points are numbered in the order 1, . . . , 9, and the points for which no capture was detected are shown by triangles in FIG. 6.

It is noted that, in this example, after nine iterations the algorithm has converged towards point 5{0.8 V, 0.75 ms}, which will be the point chosen as energy optimum. During these nine iterations, five points did not cause a capture (points No. 4, 6, 7, 8, and 9), and the backup point (point 1) was used for the counter-stimulation.

Figure 8:
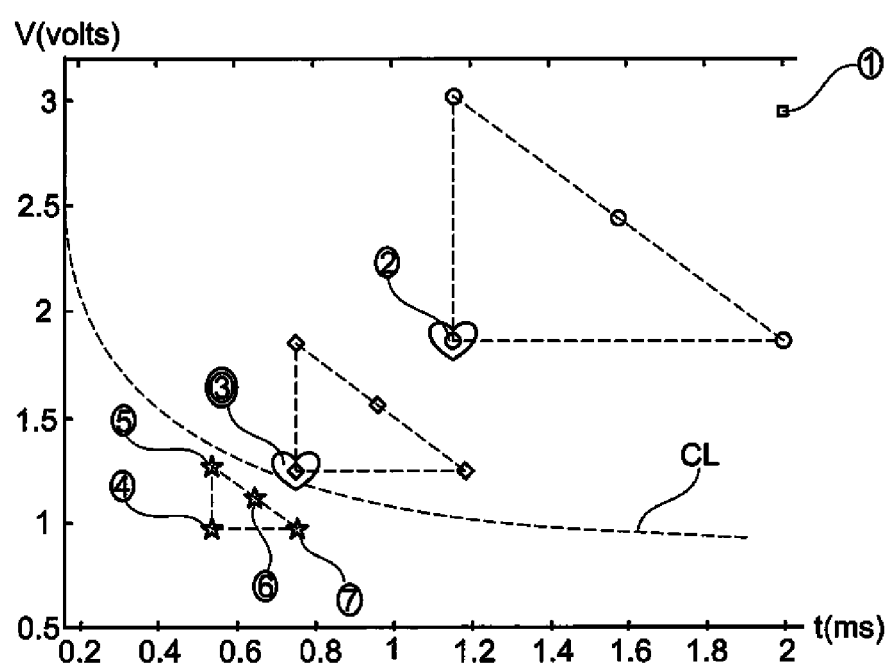
FIG. 8 is similar to FIG. 6, applied to a second illustrative implementation of the disclosure.

In FIG. 8 another example is shown, wherein the algorithm converges after seven iterations, the point finally selected as the energy optimum being point 3 (the last point with capture).

In the simplified version of the algorithm mentioned above (which consists in stopping the algorithm from the first point that does not generate capture), the algorithm ends after only four iterations, the point being selected as the energy optimum being point 3, that is to say in this case (but not necessarily, in general) the same point as in the full variant of the algorithm.

What is claimed is:

1. An active implantable medical device for stimulation, resynchronization, and/or defibrillation, comprising:
   a stimulation circuit adapted to deliver stimulation pulses to an electrode in contact with a heart of a patient;
   a capture test circuit adapted to detect a presence or an absence of a contraction of the heart subsequent to a stimulation pulse; and
   an energy adjustment circuit, wherein the energy adjustment circuit is configured to implement an iterative algorithm, wherein the iterative algorithm at each current iteration comprises testing to determine whether a contraction of the heart occurs at a plurality of energy values, wherein the testing comprises:
      setting a value of high energy, wherein the value of high energy includes a first pulse width and a first stimulation voltage;
      setting a value of low energy, wherein the value of low energy includes a second pulse width and a second stimulation voltage, wherein the second pulse width is less than the first pulse width, and wherein the second stimulation voltage is less than the first stimulation voltage;
      setting at least two intermediate energy values, each comprising a pulse width between the first and second pulse widths and a stimulation voltage between the first and second stimulation voltages;
      ranking the at least two intermediate energy values by decreasing energy value;
      delivering a stimulation pulse with the value of low energy; and
      performing a capture test to detect the presence or the absence of a contraction of the heart; and
      in the presence of a contraction:
         ending the current iteration; and
         transitioning to a new iteration, wherein the value of the delivered energy that produced the presence of a contraction is set as a new value of high energy; and
      in the absence of a contraction:
         determining whether an end of the current iteration has been reached; and
         in response to determining that the end of the current iteration has not been reached, continuing the current iteration by delivering a stimulation pulse of one of the at least two intermediate energy values, wherein the intermediate energy value of lowest rank that has not yet been delivered is selected as the intermediate energy value to be delivered.

2. The device of claim 1, wherein the energy adjustment circuit is adapted to adjust the energy of the stimulation pulses delivered by the stimulation circuit by independently controlling the stimulation voltage and the pulse width of the stimulation pulse for each stimulation pulse delivered.

3. The device of claim 1, wherein the iterative algorithm at each current iteration further comprises, in the absence of a contraction, ending the iterative algorithm.

4. The device of claim 1, wherein the iterative algorithm at each current iteration further comprises, in the absence of a contraction:
   applying consecutive counter-stimulation pulses of the first pulse width and the first stimulation voltage set for the value of high energy;
   determining whether an end of the current iteration has been reached;
   in response to determining the end of the current iteration has not been reached, continuing the current iteration with delivery of a stimulation pulse of increased energy and re-performing the capture test to detect the presence or the absence of a contraction of the heart; and
   in response to determining the end of the current iteration has been reached, selecting a last energy value that produced the presence of a contraction as a selected energy value.

5. The device of claim 4, wherein setting the at least two intermediate energy values further comprises:
   defining a first intermediate energy value comprising the second pulse width and the first stimulation voltage;
   defining a second intermediate energy value comprising the first pulse width and the second stimulation voltage;
   defining a third intermediate energy value comprising a third pulse width between the first and second pulse widths and a third stimulation voltage between the first and second stimulation voltages;
   ranking the first, second, and third intermediate energy values by decreasing energy value; and
   wherein, in the absence of a contraction and in response to determining the end of the current iteration has not been reached, continuing the current iteration comprises delivering a stimulation pulse of the first, second, or third intermediate energy value, wherein the intermediate energy value of lowest rank that has not yet been delivered is selected as the intermediate energy value to be delivered.

6. The device of claim 5, wherein the third intermediate energy value is a value such that that the third pulse width is an average of the first and second pulse widths and the third stimulation voltage is an average of the first and second stimulation voltages.

7. The device of claim 1, wherein the energy values of the stimulation pulses delivered by the stimulation circuit are at most equal to an upper energy threshold value, wherein the first pulse width and the first stimulation voltage of the value of high energy of a first iteration of the algorithm is the upper energy threshold value.

8. The device of claim 1, wherein the energy values of the stimulation pulses delivered by the stimulation circuit are at least equal to a lower energy threshold limit value with a lower pulse width and a lower stimulation voltage, wherein the low energy value is a value such that the second pulse width is an average of the first pulse width and the lower pulse width and the second stimulation voltage is an average of the first stimulation voltage and the lower stimulation voltage.

9. The device of claim 1, wherein the energy values of the stimulation pulses delivered by the stimulation circuit are between an upper energy threshold value and a lower energy threshold value calculated before each first iteration of the algorithm.

10. A method for determining an energy for stimulation, resynchronization, and/or defibrillation, comprising:
   implementing an iterative algorithm, wherein implementing each current iteration of the iterative algorithm comprises testing to determine whether a contraction of the heart occurs at a plurality of energy values, wherein the testing comprises:

setting a value of high energy, wherein the value of high energy includes a first pulse width and a first stimulation voltage;

setting a value of low energy, wherein the value of low energy includes a second pulse width and a second stimulation voltage and the second pulse width and second stimulation voltage are less than the first pulse width and first stimulation voltage;

setting at least two intermediate energy values, each comprising a pulse width between the first and second pulse widths and a stimulation voltage between the first and second stimulation voltages;

ranking the at least two intermediate energy values by decreasing energy value;

delivering a stimulation pulse with the value of low energy; and performing a capture test to detect a presence or an absence of a contraction of a heart of a patient; and in the presence of a contraction:
ending the current iteration; and
transitioning to a new iteration, wherein the value of the delivered energy that produced the presence of a contraction is set as a new value of high energy; and in the absence of a contraction:
determining whether an end of the current iteration has been reached; and
in response to determining that the end of the current iteration has not been reached, continuing the current iteration by delivering a stimulation pulse of one of the at least two intermediate energy values, wherein the intermediate energy value of lowest rank that has not yet been delivered is selected as the intermediate energy value to be delivered.

11. The method of claim 10, wherein implementing each iteration of the iterative algorithm further comprises, in the absence of a contraction, ending the iterative algorithm.

12. The method of claim 10, wherein implementing each iteration of the iterative algorithm further comprises, in the absence of a contraction:
applying consecutive counter-stimulation pulses of the first pulse width and the first stimulation voltage set for the value of high energy;
determining whether an end of the current iteration has been reached;
in response to determining the end of the current iteration has not been reached, continuing the current iteration with delivery of a stimulation pulse of increased energy and re-performing the capture test to detect the presence or the absence of a contraction of the heart; and
in response to determining the end of the current iteration has been reached, selecting a last energy value that produced the presence of a contraction as a selected energy value.

13. The method of claim 12, wherein setting the at least two intermediate energy values further comprises:
defining a first intermediate energy value comprising the second pulse width and the first stimulation voltage;
defining a second intermediate energy value comprising the first pulse width and the second stimulation voltage;
defining a third intermediate energy value comprising a third pulse width between the first and second pulse widths and a third stimulation voltage between the first and second stimulation voltages;
ranking the first, second, and third intermediate energy values by decreasing energy value; and wherein, in the absence of a contraction and in response to determining the end of the current iteration has not been reached, continuing the current iteration comprises delivering a stimulation pulse of the first, second, or third intermediate energy value, wherein the intermediate energy value of lowest rank that has not yet been delivered is selected as the intermediate energy value to be delivered.

14. The method of claim 13, wherein the third intermediate energy value is a value such that that the third pulse width is an average of the first and second pulse widths and the third stimulation voltage is an average of the first and second stimulation voltages.

15. The method of claim 10, wherein the energy values of the stimulation pulses delivered are at most equal to an upper energy threshold value, wherein the first pulse width and the first stimulation voltage of the value of high energy of a first iteration of the algorithm is the upper energy threshold value.

16. The method of claim 10, wherein the energy values of the stimulation pulses delivered are at least equal to a lower energy threshold value with a lower pulse width and a lower stimulation voltage, wherein the low energy value is a value such that the second pulse width is an average of the first pulse width and the lower pulse width and the second stimulation voltage is an average of the first stimulation voltage and the lower stimulation voltage.

17. The method of claim 10, wherein the energy values of the stimulation pulses delivered are between an upper energy threshold value and a lower energy threshold value calculated before each first iteration of the algorithm.

18. An active implantable medical device for stimulation, resynchronization and/or defibrillation, comprising:
circuitry configured to:
deliver stimulation pulses to an electrode in contact with a heart of a patient;
detect a presence or an absence of a contraction of the heart subsequent to a stimulation pulse; and
determine a selected energy by applying a plurality of iterations, wherein each current iteration comprises testing to determine whether a contraction of the heart occurs at a plurality of energy values, wherein the testing comprises:
setting a value of high energy, wherein the value of high energy includes a first pulse width and a first stimulation voltage;
setting a value of low energy, wherein the value of low energy includes a second pulse width and a second stimulation voltage and the second pulse width and second stimulation voltage are less than the first pulse width and first stimulation voltage;
setting at least two intermediate energy values, each comprising a pulse width between the first and second pulse widths and a stimulation voltage between the first and second stimulation voltages;
ranking the at least two intermediate energy values by decreasing energy value;
delivering a stimulation pulse with the value of low energy; and
performing a capture test to detect the presence or the absence of a contraction of the heart; and
in the presence of a contraction:
ending the current iteration; and
transitioning to a new iteration, wherein the value of the delivered energy that produced the presence of a contraction is set as a new value of high energy; and in the absence of a contraction:
    determining whether an end of the current iteration has been reached; and
    in response to determining that the end of the current iteration has not been reached, continuing the current iteration by delivering a stimulation pulse of one of the at least two intermediate energy values, wherein the intermediate energy value of lowest rank that has not yet been delivered is selected as the intermediate energy value to be delivered.

19. The device of claim 18, wherein each current iteration further comprises, in the absence of a contraction, ending the current iteration.

20. The device of claim 18, wherein each current iteration further comprises, in the absence of a contraction:
    applying consecutive counter-stimulation pulses of the first pulse width and the first stimulation voltage set for the value of high energy;
    determining whether an end of the current iteration has been reached;
    in response to determining the end of the current iteration has not been reached, continuing the current iteration with delivery of a stimulation pulse of increased energy and re-performing the capture test to detect the presence or the absence of a contraction of the heart; and
    in response to determining the end of the current iteration has been reached, selecting a last energy value that produced the presence of a contraction as a selected energy value.

* * * * *